United States Patent
Van Davelaar

[19]

[11] Patent Number: 6,068,766
[45] Date of Patent: *May 30, 2000

[54] APPARATUS AND METHOD FOR MAKING A SEALABLE CONNECTION TO A CHROMATOGRAPHY CARTRIDGE

[75] Inventor: Peter C. Van Davelaar, Maidens, Va.

[73] Assignee: Dyax Corporation, Cambridge, Mass.

[ * ] Notice: This patent issued on a continued prosecution application filed under 37 CFR 1.53(d), and is subject to the twenty year patent term provisions of 35 U.S.C. 154(a)(2).

[21] Appl. No.: 08/968,287

[22] Filed: Nov. 12, 1997

[51] Int. Cl.⁷ .................................................. B01D 15/08
[52] U.S. Cl. ....................... 210/198.2; 210/456; 210/656; 96/101
[58] Field of Search ..................................... 210/635, 656, 210/659, 198.2, 238, 282, 450, 456; 96/101, 106, 107

[56] References Cited

U.S. PATENT DOCUMENTS

| | | | |
|---|---|---|---|
| 3,483,986 | 12/1969 | Wright | 210/198 |
| 3,682,315 | 8/1972 | Haller | 210/233 |
| 4,093,550 | 6/1978 | Stahl et al. | 210/198 |
| 4,250,035 | 2/1981 | McDonald et al. | 210/198.2 |
| 4,283,280 | 8/1981 | Brownlee | 210/198.2 |
| 4,587,014 | 5/1986 | America | 210/198.2 |
| 4,597,866 | 7/1986 | Couillard | 210/198.2 |
| 4,719,011 | 1/1988 | Shalon et al. | 210/198.2 |
| 4,737,284 | 4/1988 | Hauke | 210/198.2 |
| 4,737,292 | 4/1988 | Ritacco et al. | 210/656 |
| 4,876,005 | 10/1989 | America | 210/198.2 |
| 4,891,133 | 1/1990 | Colvin, Jr. | 210/198.2 |
| 4,968,421 | 11/1990 | Spacek et al. | 210/198.2 |
| 4,997,465 | 3/1991 | Stanford | 55/179 |
| 5,137,628 | 8/1992 | Hart et al. | 210/198.2 |
| 5,141,635 | 8/1992 | Le Plang | 210/198.2 |
| 5,167,809 | 12/1992 | Mann et al. | 210/198.2 |
| 5,238,556 | 8/1993 | Shirkhan | 210/198.2 |
| 5,324,426 | 6/1994 | Joseph et al. | 210/198.2 |
| 5,324,427 | 6/1994 | Traveset-Masanes et al. | 210/198.2 |
| 5,366,621 | 11/1994 | Bidell | 210/198.2 |
| 5,423,982 | 6/1995 | Jungbauer | 210/198.2 |
| 5,601,708 | 2/1997 | Leavesley | 210/198.2 |

OTHER PUBLICATIONS

Pharmacia Labortory Columns, XK Column System, pp. 424–426. Undated.
Pharmacia K 50 Column p. 3 undated.

*Primary Examiner*—Ernest G. Therkorn
*Attorney, Agent, or Firm*—Fish & Richardson P.C.

[57] ABSTRACT

An apparatus and method for sealing cartridges used in liquid chromatography. Such cartridges are commonly filled with media beds that are bounded axially by porous plates. The invention involves one or two sealing heads. Each sealing head comprises two slidably connected head pieces and an elastomeric sealing member. The head pieces and the elastomeric sealing member are sized to slide easily into an open end of a cartridge when the elastomeric sealing member is uncompressed. After insertion, relative movement of the head pieces compresses the elastomeric sealing member and causes the elastomeric sealing member to expand laterally so that it forms a seal against the cartridge, when the sealing head is pressed against the media bed or porous plate.

29 Claims, 3 Drawing Sheets

APPARATUS AND METHOD FOR MAKING A SEALABLE CONNECTION TO A CHROMATOGRAPHY CARTRIDGE

BACKGROUND OF THE INVENTION

The invention relates to an apparatus and method for sealing the openings of vessels. In particular, the apparatus relates to sealing the openings of liquid chromatography cartridges.

Liquid chromatography is a technique for separating the individual compounds that exist in a subject sample. In employing the technique, the subject sample is carried in a liquid, called a mobile phase. The mobile phase carrying the subject sample is caused to migrate through a porous media, called a stationary phase. Different compounds will have differing rates of migration through the media, which effects the separation of the components in the subject sample. Liquid chromatography is commonly performed with reusable columns or with disposable cartridges, both of which are usually cylindrical, in which the media bed is bounded axially by porous plates, or plates containing defined flow paths, through which the mobile phase will flow. (See U.S. Pat. No. 4,250,035 to McDonald et al.)

Chromatography systems demand that a reliable seal be created between the column and the head through which the mobile phase enters. This is a particular problem in chromatography systems that employ disposable cartridges in which precise tolerances and careful machining that are customarily required for the creation of effective seals will increase manufacturing costs. Methods of sealing liquid chromatography cartridges typically require forcing a sealing head onto or into the cartridge. Some prior art techniques involve forcing a one-piece sealing head with an elastomeric o-ring, connected radially or to an end of the sealing head, into the cartridge. Alternately, a tapered sealing head can be forced into a cartridge without employing an o-ring to create a seal. Other prior art techniques employ o-rings or knife-edges (see U.S. Pat. No. 5,601,708 to Leavesley) oriented axially on a sealing head that create seals with the edges of the cartridges at their open ends.

Chromatography columns and cartridges also demand a close contact between the sealing heads and the media bed. Prior art sealing techniques often create gaps between the sealing head and the media bed. Even small gaps can reduce the resolution of distinct components that can be achieved. At the entrance of a column or cartridge, gaps between the sealing head and the porous plate or media will allow the subject sample to disperse and become diluted. At the exit of a column or cartridge, gaps will create a volume in which distinct fractions of the subject sample, which were separated during migration through the media, can blend back together. Thus, gaps at either end of the media bed can degrade the analytic performance of chromatography columns or cartridges.

SUMMARY OF THE INVENTION

The invention in general relates to sealing chromatography cartridges. The apparatus involves a sealing head that includes a first head piece, a second head piece, and an elastomeric sealing member. The first head piece includes a first compression face and a contact face. The second head piece includes a second compression face. The elastomeric sealing member is at least partially situated between the first and second compression faces. The first head piece, the second head piece, and the elastomeric sealing member are sized to slide easily into a chromatography cartridge having interior walls and containing a chromatography media bed that is bounded axially by porous plates.

In operation, the sealing head is inserted into the cartridge. Friction between the elastomeric sealing member and the cartridge is minimized when the elastomeric sealing member is in an uncompressed state during insertion. After the head has been inserted into the cartridge, the elastomeric sealing member is compressed between the first and second compression faces, by moving the first and second head pieces relative to each other. Compression of the elastomeric sealing member causes the elastomeric sealing member to expand laterally so that it is presses against the interior walls of the cartridge and creates a seal.

The sealing apparatus may be removed from the cartridge by moving the first head piece relative to the second head piece, thus reducing the compression forces on the elastomeric sealing member and lessening its lateral expansion. This reduces the frictional contact between the elastomeric sealing member and the interior walls of the cartridge, so that the sealing member and the first and second head pieces may be more easily removed.

By providing a second sealing apparatus, it is possible to seal both ends of a chromatography cartridge in the manner described above.

In the preferred embodiments, the first head piece contains a body portion and an outwardly-extending shoulder. The first compression face is located on the shoulder. Additionally, the first and second head pieces are shaped and sized so that the second head piece may slidably receive the body of the first head piece. The first head piece defines a flow path for the passage of a fluid, such as a mobile phase for chromatography. The contact face on the first head piece includes a slight conical concavity that helps to distribute a mobile phase uniformly to the media bed.

In operating the preferred embodiments, the contact face of the first head piece presses against the porous plate while the elastomeric sealing member is compressed axially. This axial compression causes the elastomeric sealing member to expand laterally, thus forming a seal with the interior walls cartridge.

Embodiments of the invention may include one or more of the following advantages. Insertion of the sealing apparatus into a chromatography cartridge creates minimal friction between the sealing head and the interior walls of the cartridge. Use of the sealing apparatus does not require close tolerances that create a precise fit between the sealing head and the cartridge. A small amount of force is required to create a seal with chromatography cartridges, relative to prior art methods. The sealing apparatus can be easily removed from a chromatography cartridge, so that the cartridge can be replaced. Because use of the apparatus can minimize frictional shear forces during insertion into a chromatography cartridge, wear on elastomeric sealing members is reduced. Using the apparatus can create a high quality seal. Using the apparatus can minimize the gap that is created between a sealing head and the media bed or porous plate, when sealing a chromatography cartridge. Using the apparatus can axially compress the media bed while sealing a chromatography cartridge. The apparatus has the ability to create a seal by the relative motion of two pieces that compress an elastomeric sealing member without exerting axial force on the cartridge itself. The apparatus can be adapted for sealing chromatography cartridges having media beds of varying lengths and distances from the opening of the cartridge.

Other features and advantages of the invention will be apparent from the following description of the preferred embodiments thereof and from the claims.

DESCRIPTION OF THE PREFERRED EMBODIMENTS

Figure 1:
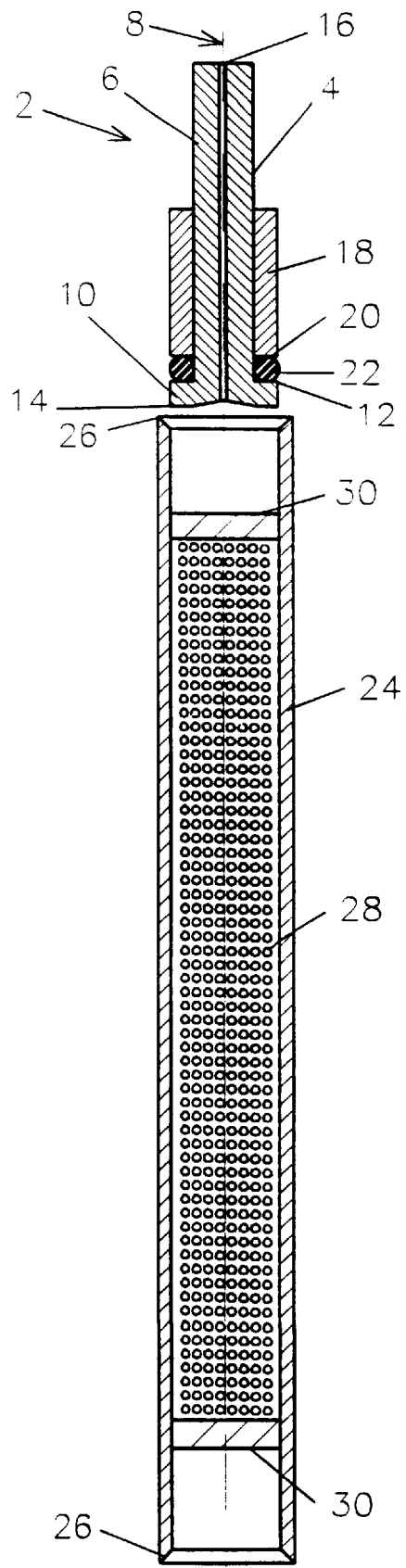
FIG. 1 is a diagrammatic cross-sectional view of a sealing apparatus according to the invention and a chromatography cartridge.
Figure 2:
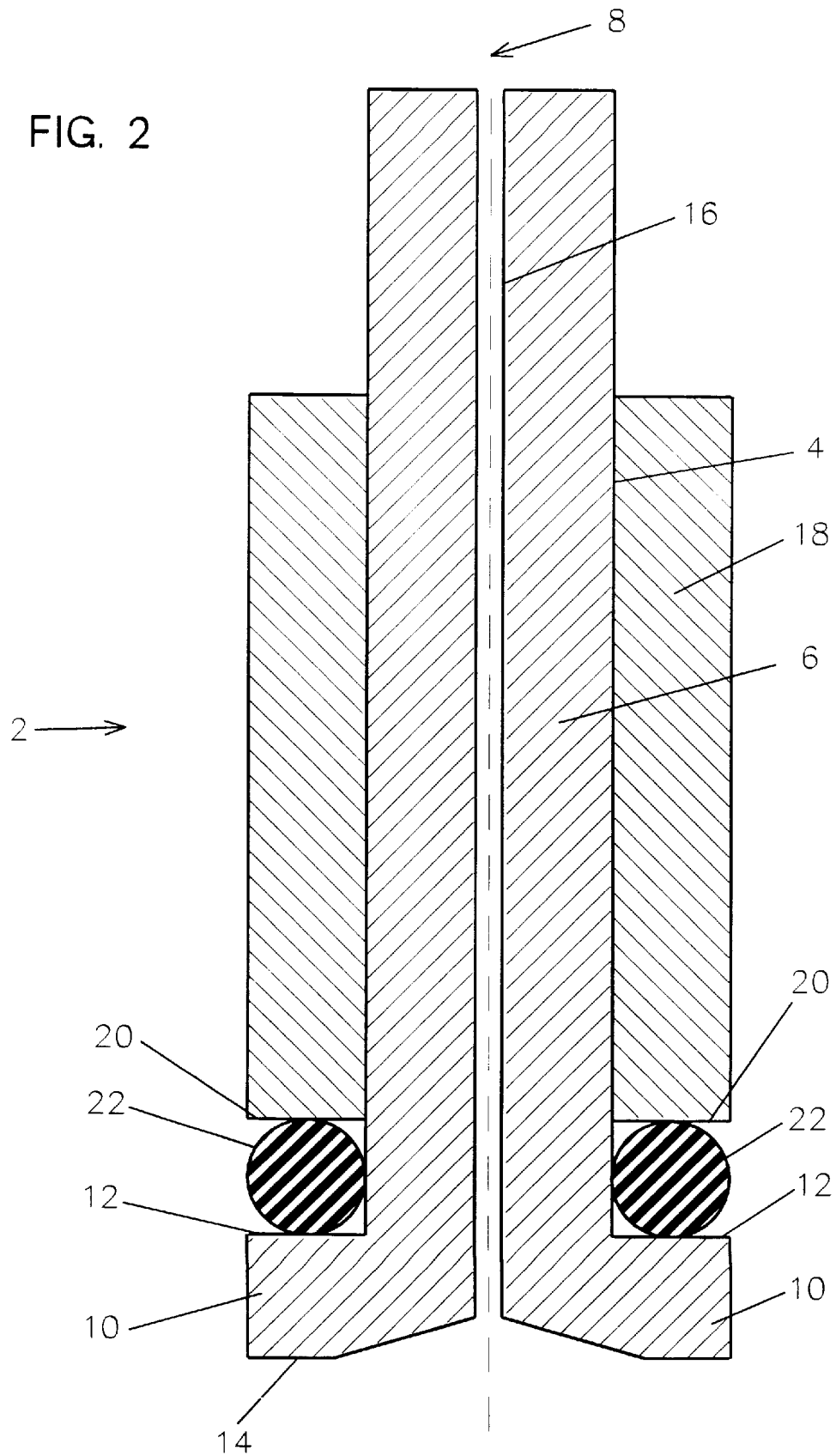
FIG. 2 is a diagrammatic cross-sectional view of a sealing apparatus according to the invention.
Figure 3:
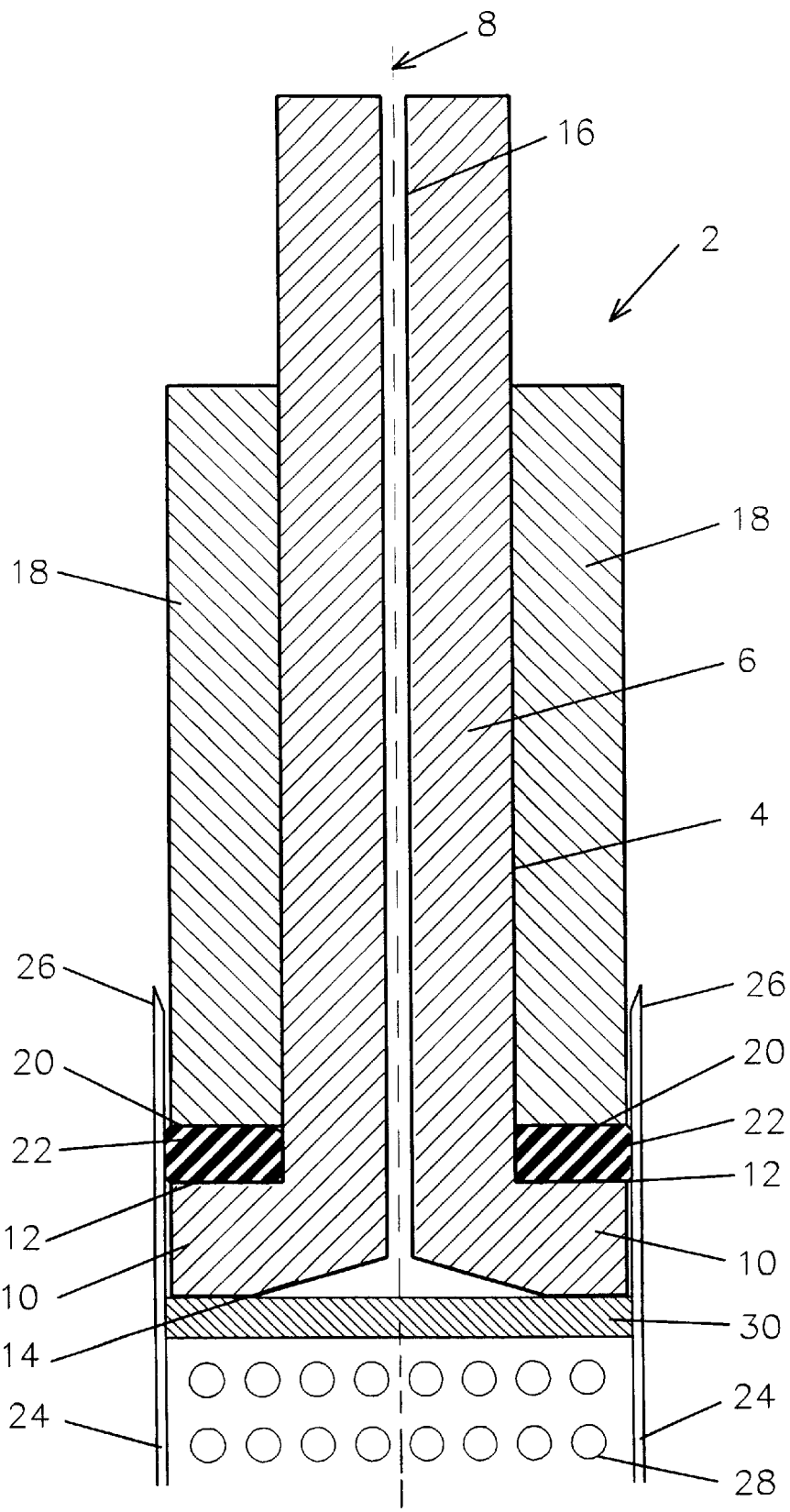
FIG. 3 is a diagrammatic cross-sectional view of a sealing apparatus according to the invention showing the formation of a seal with a chromatography cartridge.

Referring to FIGS. 1–3, there is shown a sealing apparatus employing sealing head 2, which includes first head piece 4, having body 6 with longitudinal axis 8. First head piece 4 has outwardly-extending shoulder 10, first compression face 12 that is located on shoulder 10, and contact face 14. Part of contact face 14 has a slightly conical shape or other concavity (exaggerated in FIGS. 2 and 3). First head piece 4 defines flow path 16 along axis 8. Second head piece 18, which includes second compression face 20, is sized to slidably receive body 6 of first head piece 4. Elastomeric sealing member 22 is at least partially situated between first compression face 12 and second compression face 20.

Sealing head 2 and its components are sized to fit slidably into cartridge 24, having chamfered edges 26, and chromatography media 28 bounded axially by porous plates 30.

The connection of the apparatus is shown in FIGS. 1 and 3. As shown in FIG. 1, first head piece 4, elastomeric sealing member 22, and second head piece 18 are oriented so that they may slide into cartridge 24. As shown in FIG. 3, after first head piece 4, elastomeric sealing member 22, and second head piece 18 are situated within cartridge 24, first head piece 4 and second head piece 18 are moved relative to each other, thus axially compressing elastomeric sealing member 22 between first compression face 12 and second compression face 20. The axial compression of elastomeric sealing member 22 causes it to expand laterally and press against cartridge 24, thus forming a seal.

As shown in FIG. 3, insertion of sealing head 2 can create a close connection between contact face 14 and porous plate 30. Compressing elastomeric sealing member 22 between first compression face 12 and second compression face 20, by pressing second head piece 18 against elastomeric sealing member 22, which in turn presses first head piece 4 against porous plate 30, can maintain a close connection between contact face 14 and porous plate 30 while forming a seal between sealing head 2 and cartridge 24. Thus, FIG. 3 and the related text above show that the only interaction between second head piece 18 and first head piece 4 occurs through their respective contact with elastomeric sealing member 22.

In the preferred combination, sealing head 2 is used to seal cartridge 24 having flexible walls. In other combinations, sealing head 2 is part of a containment structure assembly for receiving cartridge 24. The containment structure assembly may be pressurizable, such as a pressure vessel assembly that receives cartridge 24, compresses the flexible walls of cartridge 24, and provides uniform packing for chromatography media 28 therein. A containment structure of this type is discussed in U.S. Pat. No. 4,250,035 to McDonald, et al., which is incorporated herein by reference. Another type of pressurizable containment structure is discussed in U.S. Pat. No. 5,601,708 to Leavesley, which is also incorporated herein by reference. In other combinations, sealing head 2 is used to seal cartridge 24 having rigid walls.

Preferably, cartridge 24 is made of high-density polyethylene. However, cartridge 24 may be constructed of other materials, including glass or stainless steel. Preferably, elastomeric sealing member 22 is made of a fluorocarbon polymer, such as that sold under the trade name CHEMRAZ.

The radial displacement of the outer surface of elastomeric sealing member 22 accommodates a range of inner diameters of cartridge 24, permitting effective seals while relaxing tolerances for the inner diameter of cartridge 24 to ±0.005".

What is claimed is:

1. An apparatus for sealing a sample-conveying conduit to a chromatography cartridge containing a media bed comprising:

a first head piece and a second head piece, both of which are elongated along a longitudinal axis and are sized to fit slidably into the cartridge, said first head piece having a body, a first compression face, and a contact face, said second head piece having a second compression face and a compression force receiving member, said body defining an elongate flow channel along said axis; and an elastomeric sealing member at least part of which is situated between said first compression face and said second compression face, said elastomeric sealing member being sized to fit slidably into the cartridge when said elastomeric sealing member is not compressed, said elastomeric sealing member capable of being compressed, between said first and second compression faces, by moving said second head piece toward the media bed so that said contact face of said first head piece presses against the media bed, causing said elastomeric sealing member to expand laterally to form a seal with the cartridge, said first and second head pieces and said elastomeric sealing member disposed so that said second head piece interacts with said first head piece only through said elastomeric sealing member so that compressive force from said second head piece is transmitted through said elastomeric sealing member and through said first head piece to the media bed, when said elastomeric sealing member is compressed.

2. The apparatus of claim 1, further comprising an outwardly-extending shoulder that is part of said first head piece, said first compression face being located on said outwardly-extending shoulder.

3. The apparatus of claim 2 wherein said second head piece is sized to slidably receive said body of said first head piece.

4. The apparatus of claim 3 wherein said elastomeric sealing member is annular.

5. The apparatus of claim 4 wherein said elastomeric sealing member is an o-ring.

6. The apparatus of claim 5 wherein said contact face is at least partially concave.

7. The apparatus of claim 1 wherein said elastomeric sealing member is capable of being compressed axially, between said first and second compression faces, by the relative movement of said first and second head pieces of said sealing head so that said elastomeric sealing member expands laterally and forms a seal with the cartridge.

8. The combination of a sealing head for a sample-conveying conduit and a chromatography cartridge comprising:

a chromatography cartridge having walls;

a chromatography media bed inside said cartridge;

a first head piece and a second head piece, both of which are elongated along a longitudinal axis and are sized to fit slidably into said cartridge, said first head piece having a body, a first compression face, and a contact face adapted to contact said media bed, said second head piece having a second compression face and a compression force receiving member, said body defining an elongate flow channel along said axis; and an elastomeric sealing member at least part of which is situated between said first compression face and said second compression face, said elastomeric sealing member being sized to fit slidably into said cartridge when said elastomeric sealing member is not compressed, said elastomeric sealing member capable of being compressed, between said first and second compression faces, by moving said second head piece toward said media bed so that said contact face of said first head piece presses against said media bed and said elastomeric sealing member expands laterally to form a seal with said cartridge, said first and second head pieces and said elastomeric sealing member disposed so that said second head piece interacts with said first head piece only through said elastomeric sealing member so that compressive force from said second head piece is transmitted through said elastomeric sealing member and through said first head piece to said media bed, when said elastomeric sealing member is compressed.

9. The combination of claim 8, further comprising an outwardly-extending shoulder that is part of said first head piece, said first compression face being located on said outwardly-extending shoulder.

10. The combination of claim 9 wherein said second head piece is sized to slidably receive said body of said first head piece.

11. The combination of claim 8 wherein said elastomeric sealing member is annular.

12. The combination of claim 11 wherein said elastomeric sealing member is an o-ring.

13. The combination of claim 8 wherein said contact face is at least partially concave.

14. The combination of claim 8 wherein said cartridge has flexible walls permitting radial compression.

15. The combination of claim 8 wherein said elastomeric sealing member is capable of being compressed axially, between said first and second compression faces, by the relative movement of said first and second head pieces of said sealing head, so that said elastomeric sealing member expands laterally and forms a seal with said cartridge.

16. The combination of two sealing heads for sample-conveying conduits and a chromatography cartridge comprising:

a chromatography cartridge having walls and having a first end and a second end;

a media bed within said chromatography column having first and second outward-facing surfaces;

a first sealing head having a first head piece and a second head piece, both of which are elongated along a first longitudinal axis and are sized to fit slidably into said first end of said cartridge, said first head piece having a first body, a first compression face, and a first contact face adapted to contact said first outward-facing surface of said media bed, said second head piece having a second compression face and a first compression force receiving member, said first body defining an elongate flow channel along said first axis, said first sealing head also having a first elastomeric sealing member at least part of which is situated between said first compression face and said second compression face, said first elastomeric sealing member being sized to fit slidably into said first end of said cartridge when said first elastomeric sealing member is not compressed, said first elastomeric sealing member capable of being compressed, between said first and second compression faces, by moving said second head piece toward said media bed so that said contact face of said first head piece presses against said first outward-facing surface of said media bed, causing said first elastomeric sealing member to expand laterally to form a seal with said cartridge, said first and second head pieces and said first elastomeric sealing member disposed so that said second head piece interacts with said first head piece only through said first elastomeric sealing member so that compressive force from said second head piece is transmitted through said first elastomeric sealing member and through said first head piece to said media bed, when said first elastomeric sealing member is compressed; and a second sealing head having a third head piece and a fourth head piece, both of which are elongated along a second longitudinal axis and are sized to fit slidably into said second end of said cartridge, said third head piece having a second body, a third compression face, and a second contact face adapted to contact said second outward-facing surface of said media bed, said fourth head piece having a fourth compression face and a compression force receiving member, said second body defining an elongate flow channel along said second axis, said second sealing head also having a second elastomeric sealing member at least part of which is situated between said third compression face and said fourth compression face, said second elastomeric sealing member being sized to fit slidably into said second end of said cartridge when said second elastomeric sealing member is not compressed, said second elastomeric sealing member capable of being compressed between said third and fourth compression faces, by moving said fourth head piece toward said media bed so that said contact face of said third head piece presses against said second outward-facing surface of said media bed, causing said second elastomeric sealing member to expand laterally to form a seal with said cartridge, said third and fourth head pieces and said second elastomeric sealing member disposed so that said fourth head piece interacts with said third head piece only through said second elastomeric sealing member so that compressive force from said fourth head piece is transmitted through said second elastomeric sealing member and through said third head piece to said media bed, when said second elastomeric sealing member is compressed.

17. The combination of claim 16, further comprising:

a first outwardly-extending shoulder that is part of said first head piece, said first compression face being located on said first outwardly-extending shoulder; and a second outwardly-extending shoulder that is part of said third head piece, said third compression face being located on said second outwardly-extending shoulder.

18. The combination of claim 17 wherein said second head piece is sized to slidably receive said first body of said first head piece and said fourth head piece is sized to slidably receive said second body of said third head piece.

19. The combination of claim 16 wherein said first and second elastomeric sealing members are annular.

20. The combination of claim 19 wherein said first and second elastomeric sealing members are o-rings.

21. The combination of claim 16 wherein said first and second contact faces are each at least partially concave.

22. The combination of claim 16 wherein:

said first elastomeric sealing member is capable of being compressed axially, between said first and second compression faces, by the relative movement of said first and second head pieces of said first sealing head, so that said first elastomeric sealing member expands laterally and forms a seal with said cartridge; and said second elastomeric sealing member is capable of being compressed axially, between said third and fourth compression faces, by the relative movement of said third and fourth head pieces of said second sealing head, so that said second elastomeric sealing member expands laterally and forms a seal with said cartridge.

23. The combination of claim 16 wherein said cartridge has flexible walls permitting radial compression.

24. An apparatus for sealing a vessel containing a media bed comprising:

a first head piece and a second head piece, both of which are sized to fit slidably into the vessel, said first head piece having a body, a first compression face, and a contact face adapted to contact the media bed, said second head piece having a second compression face and a compression force receiving member; and an elastomeric sealing member at least part of which is situated between said first compression face and said second compression face, said elastomeric sealing member being sized to fit slidably into the vessel when not compressed, said elastomeric sealing member capable of being compressed, between said first and second compression faces, by moving said second head piece toward the media bed so that said contact face of said first head piece presses against the media bed, causing said elastomeric sealing member to expand laterally to form a seal with the vessel, said first and second head pieces and said elastomeric sealing member disposed so that said second head piece interacts with said first head piece only through said elastomeric sealing member so that compressive force from said second head piece is transmitted through said elastomeric sealing member and through said first head piece to the media bed, when said elastomeric sealing member is compressed.

25. The apparatus of claim 24, further comprising an outwardly-extending shoulder that is part of said first head piece, said first compression face being located on said outwardly-extending shoulder.

26. The apparatus of claim 25 wherein said second head piece is sized to slidably receive said body of said first head piece.

27. The apparatus of claim 26 wherein said elastomeric sealing member is annular.

28. The apparatus of claim 27 wherein said elastomeric sealing member is an o-ring.

29. The apparatus of claim 24 wherein said elastomeric sealing member is capable of being compressed axially, between said first and second compression faces, by the relative movement of said first and second head pieces of said sealing head, so that said elastomeric sealing member expands laterally and forms a seal with the vessel.

* * * * *